United States Patent
Prince

Patent Number: 5,797,883
Date of Patent: Aug. 25, 1998

[54] MEDICAL DEVICE FOR REMOVAL OR INJECTION OF BIOLOGICAL MATERIAL BY REMOTE CONTROL

[76] Inventor: Jean-Claude Prince, 72, rue du Vexin, 60530 Ercuis, France

[21] Appl. No.: 374,951

[22] Filed: Jan. 19, 1995

[30] Foreign Application Priority Data

Jan. 19, 1994 [FR] France ................. 94 00545

[51] Int. Cl.⁶ .................................. A61M 5/178
[52] U.S. Cl. ........................... 604/170; 604/171
[58] Field of Search ..................... 606/170, 171, 606/149, 152

[56] References Cited

U.S. PATENT DOCUMENTS

| | | |
|---|---|---|
| 3,088,454 | 5/1963 | Shute . |
| 4,529,399 | 7/1985 | Groshong ................. 604/170 |
| 4,757,827 | 7/1988 | Buchbinder ............... 604/170 |
| 4,808,158 | 2/1989 | Kreuzer .................. 604/170 |
| 5,069,224 | 12/1991 | Zinnanti, Jr. . |
| 5,183,470 | 2/1993 | Wettermann . |
| 5,242,418 | 9/1993 | Weinstein ................ 604/182 |

FOREIGN PATENT DOCUMENTS

| | | |
|---|---|---|
| 935625 | 10/1995 | Germany . |
| 2256369 | 12/1992 | United Kingdom . |
| WO8606951 | 12/1986 | WIPO . |

*Primary Examiner*—Michael A. Brown
*Attorney, Agent, or Firm*—Weiser and Associates, P.C.

[57] ABSTRACT

A device for sampling biological materials having a tube having a front segment and rear segment, wherein the outer diameter of the front segment is smaller than the outer diameter of the rear segment. The inner diameter of the front segment is smaller than the inner diameter of the rear segment. The front segment has a distal opening. A rod having a piston having an outer diameter substantially equal to the inner diameter of the rear segment, wherein the rod is engaged within the tube, the piston is positioned within the rear segment, such that when the rod is partially withdrawn from the tube, a negative pressure is created in the front segment that is greater than the negative pressure created within part of the rear segment by the partial withdrawal of the rod, thereby enabling the sampling of the biological materials through the distal opening.

17 Claims, 1 Drawing Sheet

MEDICAL DEVICE FOR REMOVAL OR INJECTION OF BIOLOGICAL MATERIAL BY REMOTE CONTROL

The present invention relates to a device for medical use for removal or injection by remote control, of the type including a tube and a rod movable within the interior of the tube. The invention relates to a sampling device formed by a catheter tube of very small cross section to enable its non-invasive, non-traumatizing introduction by natural routes, particularly for applications in the field of gynecology. The object of the invention is to improve the performance of the sampling devices made in the form of flexible catheter tubes with a rod, by increasing the ratio between the sampling capacity and the external cross section of the tube.

In the prior art, devices of this kind are known that are intended particularly for taking samples in such organs as the lung, blood vessels, and viscera, and for taking endouterine samples. The tube is constituted by a flexible catheter tube of very slight diameter to enable passage through natural routes in a non-invasive and non-traumatizing manner. The term "snap ring" in the sense of the present patent is understood to mean any elongated flexible element capable of being introduced into the inside of the tube.

The devices in the prior art are constituted of an outer tube and a rod provided with a piston. The tube is introduced by a natural route and is pushed in until the end of the tube arrives at the level of the zone where sampling is to be done. The physician then exerts traction on the end of the rod extending outside the tube. The piston creates negative pressure and causes mucus and cells to be aspirated into the inside of the tube.

The device is then withdrawn, and the sample is recovered by pushing the piston, for histological and cytological analysis of the sample.

The devices of the prior art cannot be used, however, when the introduction route is smaller than 2.8 mm or has a shrinkage of cross section less than the external cross section of the tube. To overcome this difficulty for sampling in organs that open through natural routes of very small cross section, the prior art has proposed using puncturing needles. The devices for sampling with such needles are described in the following patents, by way of example: PCT WO 86/06951, GB 2 256 369, U.S. Pat. No. 3,088,454, German Patent 935 625, or U.S. Pat. No. 5,183,470. These devices are not satisfactory, because they involve more traumatic intervention than when flexible devices are used.

Reducing the diameter of the devices to a flexible capillary tube is no longer an appropriate solution, because it would mean an inadequate internal volume for obtaining a void sufficient to assure aspiration of the sample, and it would be deleterious to the mechanical qualities of the assembly.

The object of the invention is to overcome the disadvantages discussed above by proposing a device for sampling through natural routes of very small cross section, nevertheless permitting sampling of quantities of biological material sufficient for purposes of histological or cytological analyses.

To that end, the invention relates more particularly to a device characterized in that the tube has a rear segment having an internal diameter substantially equal to the external diameter of the piston and a front segment having an internal cross section less than the internal cross section of the rear segment and greater than the external cross section of the rod, the piston being fixed on the rod at a position enabling the introduction of the front portion of the rod into the front segment of the tube, the front segment having an opening for communication with the external surroundings.

The vacuum is achieved in the segment having the larger cross section and is transmitted into the front segment having the smaller cross section. This segment of smaller cross section is plugged when at rest by the end of the rod, which prevents the penetration of fluids or air prior to the aspiration.

Advantageously, the rear segment has an annular or right-angle stop whose internal cross section is less than the external cross section of the piston.

In a first variant, the front segment has at least one lateral distal opening on its end.

In a second variant, the front segment has at least one frontal distal opening on its end.

In a particular embodiment, the device further includes a tubular element whose rigidity is greater than the rigidity of the tube and whose internal cross section is larger than the external cross section of the tube and whose length is greater than the length of the front segment.

This embodiment makes it possible to guide the front segment into the cavities.

Preferably, this embodiment further employs a front segment made of an elastically deformable material with shape memory.

The invention will be better understood from reading the ensuing description in conjunction with the accompanying drawings.

Figure 1:
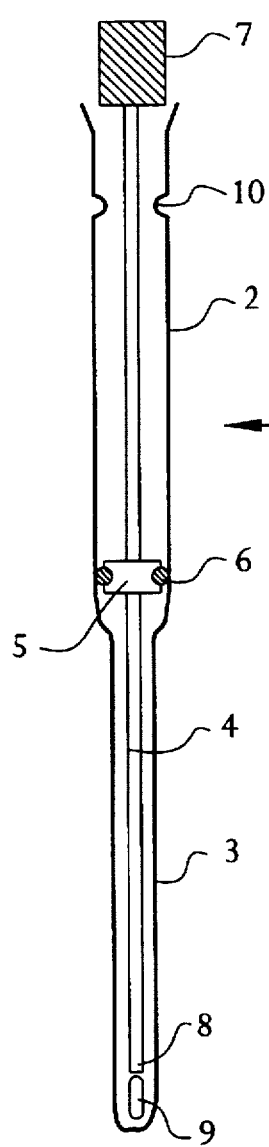
FIG. 1 is a longitudinal sectional view of the device in accordance with the first embodiment.

The device is constituted by only two pieces, namely a semi-rigid or flexible catheter (1) and a semi-rigid rod (4), both of them of plastic material for medical use.

The device (1) is constituted by a single tubular element of plastic material, deformed so as to have a rear segment (2) and a front segment (3). It is formed by a catheter made of a single piece of polypropylene or flexible methacrylate, or of any other material known in this field of the art for making material for medical usage. It is made by stretching part of a tube whose cross section is initially constant, so that the tube then has two consecutive segments of different cross sections.

A semi-rigid rod (4) is positioned on the interior of the tube (1). The length of this rod (4) is greater than the length of the tube (1), and its rear end is provided with a handle (7) enabling the physician to exert traction on the rod (4). In the way as for the tube, the rod is constituted by an element of solid plastic material, part of which has a bulge forming the piston (5). This bulge may be obtained by stretching the element of plastic material on either side of the part forming the piston.

The rod is provided with a piston (5) surrounded by a toroidal sealing ring (6) having an external diameter substantially equal to the diameter of the rear segment (2).

This piston (5) is placed on the rod (4) in such a way as to come just to the rear of the transition zone between the front segment (3) and the rear segment (2) when the rod (4) is pushed all the way into the tube (1). The difference between the end (8) of the rod (4) and the piston (5) is thus substantially equivalent to the length of the front segment (3).

The front segment additionally has a lateral distal opening (9) in proximity with its rear end.

When the physician withdraws the rod (4) as far as the stop (10), he creates a negative pressure corresponding to the volume of the rear segment (2) cleared by the displacement of the piston (5), whose end must remain inside the segment (2).

This negative pressure has repercussions in the front segment. The negative pressure created at the level of the opening (9) corresponds to the negative pressure in the rear segment, multiplied by the ratio between the cross section of the rear segment (2) and the cross section of the front segment (3).

The rear segment moreover has an annular or right-angle stop (10) that prevents the inopportune withdrawal of the rod (4).

Figure 2:
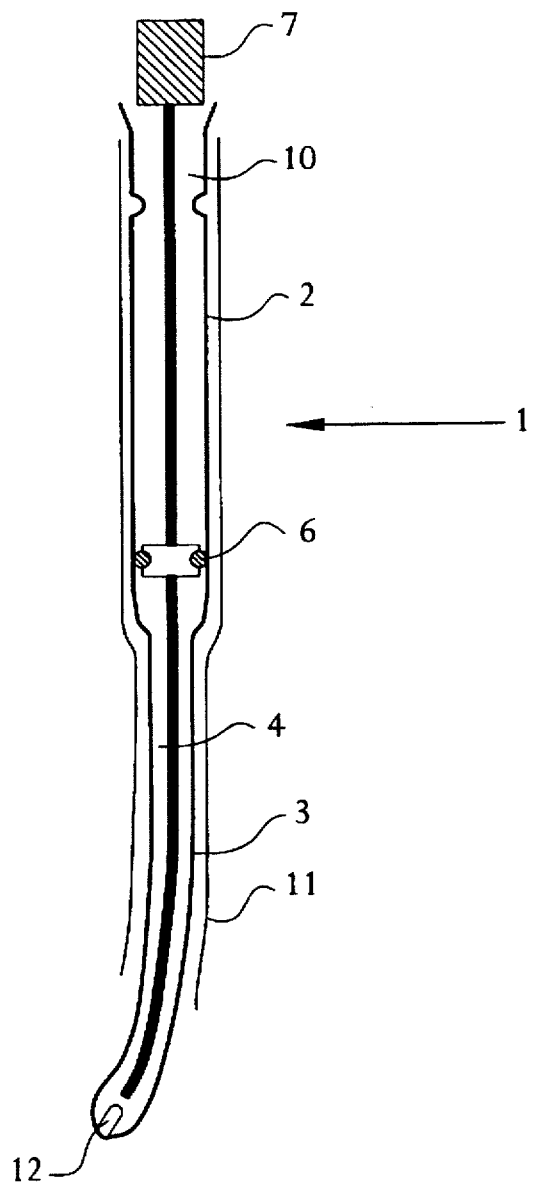
FIG. 2 is a longitudinal sectional view of the device in accordance with a second embodiment.

FIG. 2 shows a variant embodiment, in which the tube is introduced into an outer tube (11) of greater rigidity, and having a shoulder (12).

The length of the outer tube (11) is greater than the length of the rear segment (2), and is less than the total length of the tube, so as to enable a relative displacement of the tube (1) with respect to the outer tube (11) by way of action upon the rear portion of the outer tube (11).

The front segment (3) at least is made of a material that retains shape memory and that at rest has a curved shape. When it is engaged within the outer tube (11), the front segment comes into alignment with the rear segment (2) so as to form a straight tube. The physician can then exert traction on the outer tube (11) in order to release the front segment from any transverse constraint. The front segment then resumes the curved shape, making it possible to reach sampling zones that are inaccessible to a straight tube. In this embodiment, the opening (12) is frontal. By way of example, the length of the front segment is 130 mm, the inside diameter is 1.5 mm, and the external diameter is 1.95 mm. The length of the rear segment is 137 mm, the internal diameter is 2.6 mm, and the external diameter is 3.7 mm. The length of the rod is 298 mm, and its diameter is 1.5 mm. On its rear end, it has an enlarged handle portion 25 mm in length. The piston extends over a length of 1 mm.

The device is manufactured in the following way:

Beginning with a tube made by extrusion, lengths of tubing of circular cross section are prepared, having a length less than the length of the final device and having an external cross section substantially equal to the final cross section of the rear segment. One of the ends of each length of tubing is cut on a diagonal, and a rigid steel wire whose cross section is substantially equal to the inside cross section of the front segment is threaded into the length of tubing.

Next, the length of tubing thus prepared is introduced into a heated die that has a conical orifice whose inlet cross section is substantially equal to the external cross section of the length of tubing, and whose outlet cross section is substantially equal to the final cross section of the front segment. Cutting one of the ends on the diagonal makes it easier to introduce the length of tubing into the die. The length of tubing is pulled through the die over a length substantially equal to the length of the front segment. The temperature of the die is substantially equal to and in any case greater than the softening temperature (Vicat point) of the material constituting the length of tubing, so as to obtain an irreversible extrusion rather than an elastic deformation.

The tube thus prepared is then baked at 90° for approximately 30 minutes.

Next, the graduations are marked on the front segment, and the front end is closed with a heated mold against which the front end is mashed. The distal opening is made with the aid of a hollow punch. The graduations are also marked on the front segment.

The rod is also prepared by extrusion. The piston is made by duplicate molding. After the rod has been introduced into the outer tube, the rear end of the tube is mashed against a heated mold in such a way as to partly crimp the rear edge in order to form a shoulder in the form of a flange.

I claim:

1. A method for manufacturing a device for remote sampling for medical use, characterized in that a length of tubing whose length is less than the length of the final device and whose external cross section is substantially equal to the final cross section of the rear segment is cut from a tube made by extrusion; a rigid steel wire whose cross section is substantially equal to the internal cross section of the front segment is threaded into the length of tubing; next, the length of tubing thus prepared is introduced into a heated die having a conical orifice whose inlet cross section is substantially equal to the external cross section of the length of tubing, and whose outlet cross section is substantially equal to the final cross section of the front segment; and the length of tubing is pulled through the die over a length substantially equal to the length of the front segment.

2. A method for manufacturing a remote sampling device for medical use as defined by claim 1, characterized in that the front end is closed with a heated mold against which the front end is mashed; the distal opening is made with the aid of a hollow punch; and the graduations are also marked on the front segment.

3. A method for manufacturing a remote sampling device for medical use as defined by claim 1 or 2, characterized in that a rod likewise prepared by extrusion, having a piston made by duplicate molding, is introduced into the tubular element.

4. A method for manufacturing a remote sampling device for medical use as defined by claim 1, characterized in that the rear end of the tube is mashed against a heated mold in such a way as to partly crimp the rear edge in order to form a shoulder in the form of a collar, after introduction of the rod into the outer tube.

5. A device for sampling biological materials, comprising:
    (a) a tube having a front segment and a rear segment, wherein:
        the outer diameter of the front segment is smaller than the outer diameter of the rear segment;
        the inner diameter of the front segment is smaller than the inner diameter of the rear segment; and
        the front segment has a distal opening;
    (b) a rod having a piston having an outer diameter substantially equal to the inner diameter of the rear segment, wherein, when the rod is engaged within the tube, the piston is positioned within the rear segment, such that, when the rod is partially withdrawn from the tube, a negative pressure is created in the front segment that is greater than the negative pressure created within part of the rear segment by the partial withdrawal of the rod, thereby enabling sampling of the biological materials through the distal opening; and
    (c) an outer tube of rigidity greater than that of the tube, such that when the tube and rod are engaged within the outer tube, the tube and the rod obtain the shape of the outer tube.

6. The device of claim 1, wherein the tube is composed of a semi-rigid or flexible material to enable easy insertion of the device through a natural route, and the rod is composed of a semi-rigid material.

7. The device of claim 5, wherein the distal opening is either a lateral opening or a frontal opening.

8. The device of claim 5, wherein the rear segment of the tube has a stop that prevents inopportune full withdrawal of the rod from the tube.

9. The device of claim 1, wherein the front segment of the tube has a curved shape at rest, such that, when front segment extends beyond the length of the outer tube, the front segment curves to enable reaching of sampling zones that are inaccessible to the more rigid outer tube.

10. The device of claim 5, wherein the rod is adapted to be withdrawn such that the sampled biological materials are retained in both the front segment and a portion of the rear segment, thereby enabling sampling of sufficient quantities of the biological materials.

11. The device of claim 5, wherein the device is adapted to operate without any puncturing needles.

12. The device of claim 5, wherein the distal opening is plugged by the end of the rod, when the rod is fully engaged within the tube.

13. The device of claim 5, wherein the piston comprises a bulge in the rod and toroidal sealing ring.

14. A method for manufacturing a tube for a device for sampling biological materials, the tube having a front segment and a rear segment, wherein the outer diameter of the front segment is smaller than the outer diameter of the rear segment, and the inner diameter of the front segment is smaller than the inner diameter of the rear segment, the method comprising the steps of:

(a) providing a single piece of tube material whose cross section is substantially equal to the cross section of the rear segment; and (b) stretching part of the single piece of tube material to form the front segment.

15. The method of claim 14, wherein step (b) comprises the step of introducing the tube material into a heated die having a conical orifice whose outlet cross section is substantially equal to the external cross section of the front segment.

16. The method of claim 15, wherein one end of the tube material is cut on a diagonal to facilitate introduction of the tube material into the die.

17. A device for sampling biological materials, comprising:

(a) a tube having a front segment and a rear segment, wherein:
   the outer diameter of the front segment is smaller than the outer diameter of the rear segment;
   the inner diameter of the front segment is smaller than the inner diameter of the rear segment; and
   the front segment has a distal opening;

(b) a rod having a piston having an outer diameter substantially equal to the inner diameter of the rear segment, wherein, when the rod is engaged within the tube, the piston is positioned within the rear segment, such that, when the rod is partially withdrawn from the tube, a negative pressure is created in the front segment that is greater than the negative pressure created within part of the rear segment by the partial withdrawal of the rod, thereby enabling sampling of the biological materials through the distal opening, wherein the piston comprises a bulge in the rod and toroidal sealing ring.

* * * * *